US009675425B2

(12) United States Patent
Oppenheimer

(10) Patent No.: US 9,675,425 B2
(45) Date of Patent: Jun. 13, 2017

(54) APPARATUS FOR ALIGNING A DENTAL DRILL

(71) Applicant: Benjamin D. Oppenheimer, Williamsville, NY (US)

(72) Inventor: Benjamin D. Oppenheimer, Williamsville, NY (US)

(*) Notice: Subject to any disclaimer, the term of this patent is extended or adjusted under 35 U.S.C. 154(b) by 0 days.

(21) Appl. No.: 15/053,219

(22) Filed: Feb. 25, 2016

(65) Prior Publication Data

US 2016/0256236 A1  Sep. 8, 2016

Related U.S. Application Data

(60) Provisional application No. 62/126,885, filed on Mar. 2, 2015.

(51) Int. Cl.
*A61C 1/08* (2006.01)
(52) U.S. Cl.
CPC .................... *A61C 1/084* (2013.01)
(58) Field of Classification Search
CPC ........... A61C 1/084; A61C 1/085; A61C 3/02; A61C 8/0089
USPC ..................................... 433/75, 76
See application file for complete search history.

(56) References Cited

U.S. PATENT DOCUMENTS

| | | |
|---|---|---|
| 1,189,753 A | 7/1916 | Thue |
| 3,011,259 A | 5/1959 | Baum |
| 3,664,022 A | 5/1972 | Small |
| 3,895,444 A | 7/1975 | Small |
| 4,177,565 A | 12/1979 | Heasley |
| 4,364,381 A | 12/1982 | Sher et al. |
| 5,439,381 A * | 8/1995 | Cohen ............... A61C 8/001 433/173 |
| 5,688,283 A | 11/1997 | Knapp |
| 5,833,693 A | 11/1998 | Abrahami |
| 5,888,065 A | 3/1999 | Sussman |
| 6,062,856 A | 5/2000 | Sussman |
| 6,626,667 B2 | 9/2003 | Sussman |
| 6,869,283 B2 | 3/2005 | Sussman |
| 6,881,059 B2 | 4/2005 | Wennemann |
| 7,104,795 B2 | 9/2006 | Dadi |

(Continued)

FOREIGN PATENT DOCUMENTS

JP        2007209739 A        8/2007

*Primary Examiner* — Nicholas Lucchesi
(74) *Attorney, Agent, or Firm* — Simpson & Simpson, PLLC

(57) ABSTRACT

An apparatus for aligning a dental drill including a guide body having a drill guide through hole including a longitudinal axis, a pair of guide pincer axes orthogonal to and symmetrical about the longitudinal axis and a pair of outer pincer axes orthogonal to and symmetrical about the longitudinal axis, a pair of opposed outer pincers, each outer pincer having an outer engagement protrusion, and each outer pincer is rotatable about a respective one of the pair of outer pincer axes, and a pair of opposed guide pincers, each guide pincer having gear teeth and a guide engagement protrusion, and each guide pincer is rotatable about a respective one of the pair of guide pincer axes. The gear teeth of each guide pincer engage the gear teeth of the other, guide pincer, rotation of one of the pair of guide pincers causes rotation of the other of the pair of guide pincers and the pair of opposed outer pincers rotate independent of each other.

11 Claims, 6 Drawing Sheets

(56) References Cited

U.S. PATENT DOCUMENTS

| | | |
|---|---|---|
| 7,654,823 B2 | 2/2010 | Dadi |
| 7,905,726 B2 | 3/2011 | Stumpel |
| 8,123,752 B2* | 2/2012 | Zucherman ........ A61B 17/7062 606/86 R |
| 8,714,975 B2 | 5/2014 | Stumpel |
| 8,764,763 B2 | 7/2014 | Wong et al. |
| 8,794,963 B2 | 8/2014 | Lancieux et al. |
| 2003/0134252 A1 | 7/2003 | Sussman |
| 2004/0013999 A1 | 1/2004 | Sussman |
| 2005/0245936 A1* | 11/2005 | Tuke .................... A61B 17/175 606/89 |
| 2007/0276400 A1 | 11/2007 | Moore et al. |
| 2009/0202959 A1 | 8/2009 | Ajlouni et al. |
| 2010/0311006 A1 | 12/2010 | Lancieux et al. |
| 2011/0287381 A1* | 11/2011 | Sanders ................ A61C 1/084 433/75 |
| 2014/0093838 A1 | 4/2014 | Carmichael et al. |
| 2014/0193769 A1 | 7/2014 | Mackey |
| 2014/0193770 A1 | 7/2014 | Mackey |
| 2014/0193772 A1 | 7/2014 | Mackey |
| 2015/0351865 A1* | 12/2015 | Honig .................. A61C 8/0053 433/76 |
| 2016/0081765 A1* | 3/2016 | Sanders ................ A61C 1/084 433/75 |
| 2016/0317247 A1* | 11/2016 | Katto .................... A61C 1/085 |

\* cited by examiner

APPARATUS FOR ALIGNING A DENTAL DRILL

CROSS-REFERENCE TO RELATED APPLICATIONS

This patent application claims the benefit under 35 U.S.C. §119(e) of U.S. Provisional Patent Application No. 62/126,885, filed Mar. 2, 2015, which application is incorporated herein by reference.

TECHNICAL FIELD

The presently disclosed embodiments are directed to providing an apparatus for aligning a dental drill, and more particularly to an apparatus for aligning a dental drill which locates a drill guide based on a particular configuration of a patient jawbone, and even more particularly to an apparatus for aligning a dental drill which locates a drill guide by direct or indirect contact between the apparatus and a patient jawbone.

BACKGROUND

Dental restoration takes a variety of forms. In some instances, a dentist or dental technician must determine the location of a patient's jawbone for subsequent drilling operations. For example, prior to placing and securing an implant, an initial hole must be formed in the jawbone. The hole provides a location to seat an implant, a post, etc.

Locating and drilling a jawbone is difficult as every jawbone is unique in shape. The circumstance is further complicated as gum tissue or the position thereof may not be a valid measure of the underlying shape of the concealed jawbone. Although imaging techniques, e.g., X-ray imaging, may be used to gain a general understanding of the shape of the jawbone, the final placement and alignment of a drill is difficult based on prior obtained images alone. Still further, jawbones are typically more narrow and irregular in the region towards the upper portions, i.e., the regions where teeth are connected to the jawbone. The irregular shape and thickness in combination with the inability to predict the jawbone location, creates a need for an apparatus to align a dental drill prior to operation.

Failing to properly align a drill can result in the drill inadvertently exiting the side of the jawbone, or in extreme circumstances, can result in the jawbone being damaged such that subsequent attachment of a dental implant is extremely difficult or not possible.

The present disclosure sets forth an apparatus which addresses these difficulties in a repeatable and practical manner.

SUMMARY

Broadly, the subject invention comprises a dental drill alignment guide. The apparatus includes two pairs of opposed pincers that locate the jawbone and align the apparatus to the same for subsequent drilling operations. The movement of the upper or guide pincers is controlled by a geared connection between the opposing pincers, while the frame or outer pincers move independent of each other. After the apparatus is secured to a patient's jawbone, the drill guide, located at the top center of the apparatus, is used to guide a drill bit into the jawbone to minimize or eliminate the possibility of the drill bit exiting the side of the jawbone and causing pain, discomfort, etc. to the patient.

According to aspects illustrated herein, there is provided an apparatus for aligning a dental drill including a guide body having a drill guide through hole including a longitudinal axis, a pair of guide pincer axes orthogonal to and symmetrical about the longitudinal axis and a pair of outer pincer axes orthogonal to and symmetrical about the longitudinal axis, a pair of opposed outer pincers, each outer pincer having an outer engagement protrusion, and each outer pincer is rotatable about a respective one of the pair of outer pincer axes, and a pair of opposed guide pincers, each guide pincer having gear teeth and a guide engagement protrusion, and each guide pincer is rotatable about a respective one of the pair of guide pincer axes. The gear teeth of each guide pincer engage the gear teeth of the other guide pincer, rotation of one of the pair of guide pincers causes rotation of the other of the pair of guide pincers and the pair of opposed outer pincers rotate independent of each other.

Other objects, features and advantages of one or more embodiments will be readily appreciable from the following detailed description and from the accompanying drawings and claims.

BRIEF DESCRIPTION OF THE DRAWINGS

Various embodiments are disclosed, by way of example only, with reference to the accompanying drawings in which corresponding reference symbols indicate corresponding parts, in which.

DETAILED DESCRIPTION

Figure 1:
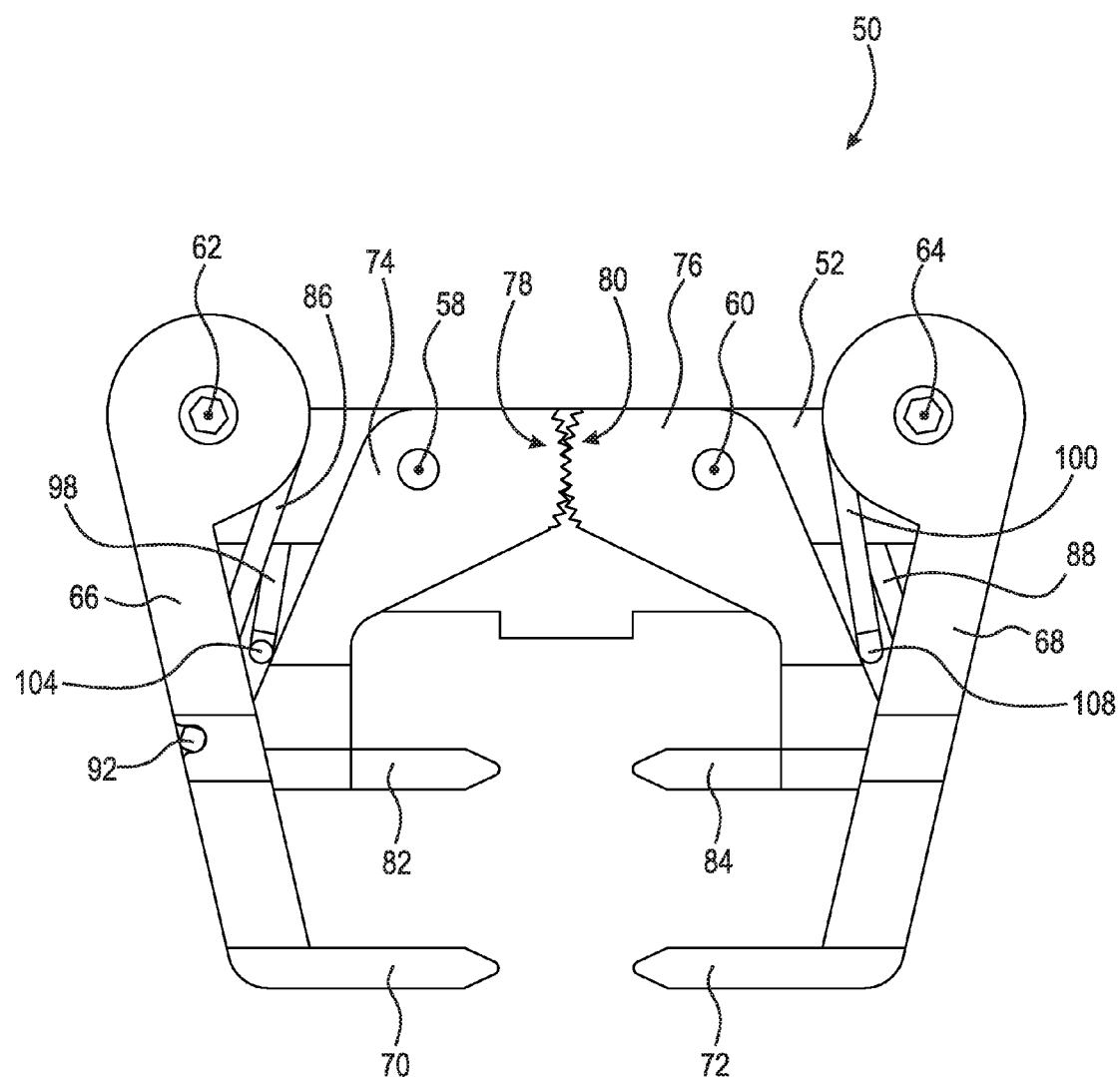
FIG. 1 is a side elevational view of an embodiment of a present apparatus for aligning a dental drill shown in a closed arrangement.
Figure 2:
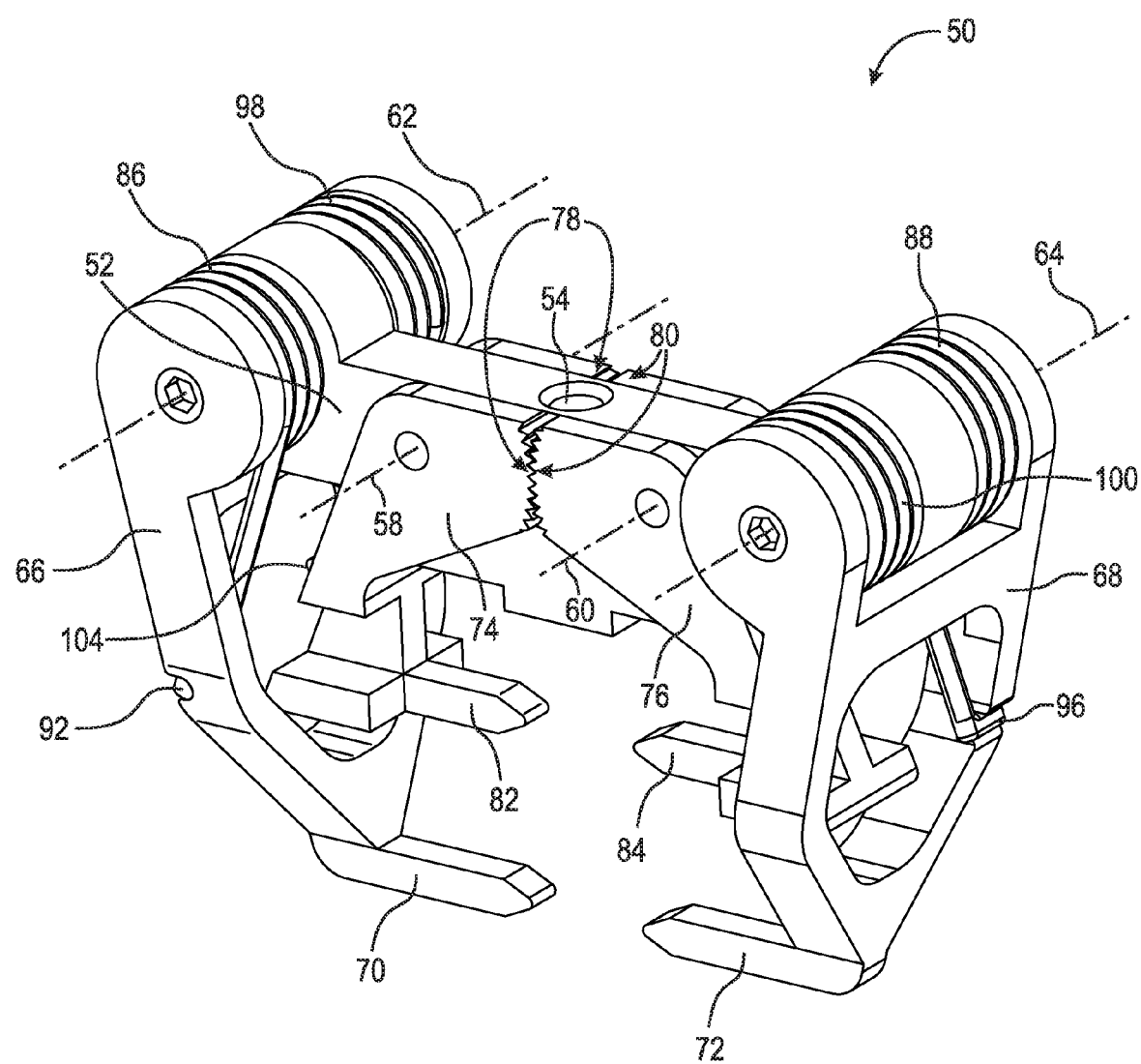
FIG. 2 is a perspective view of the present apparatus of FIG. 1 also shown in a closed arrangement.
Figure 3:
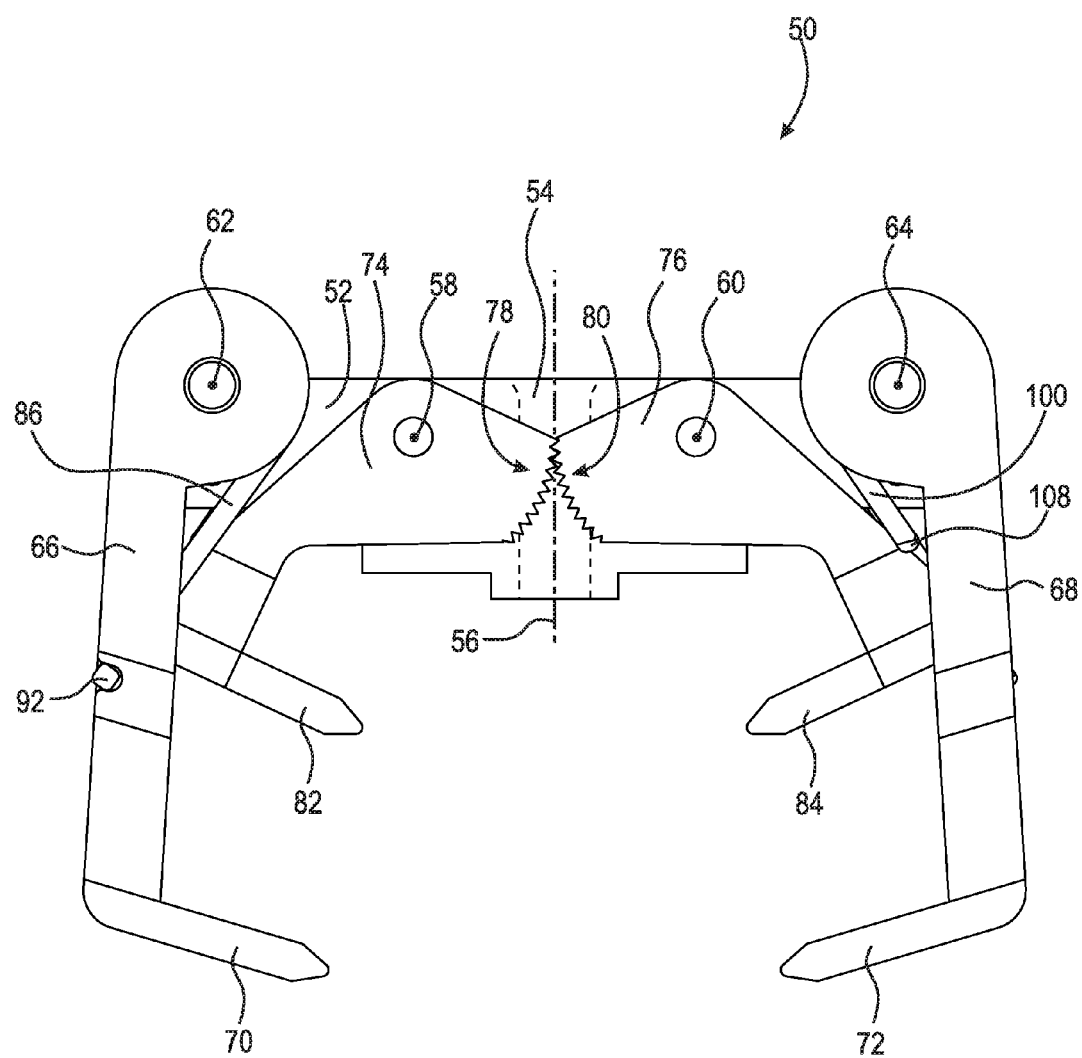
FIG. 3 is a side elevational view of the present apparatus of FIG. 1 shown in an open arrangement.
Figure 4:
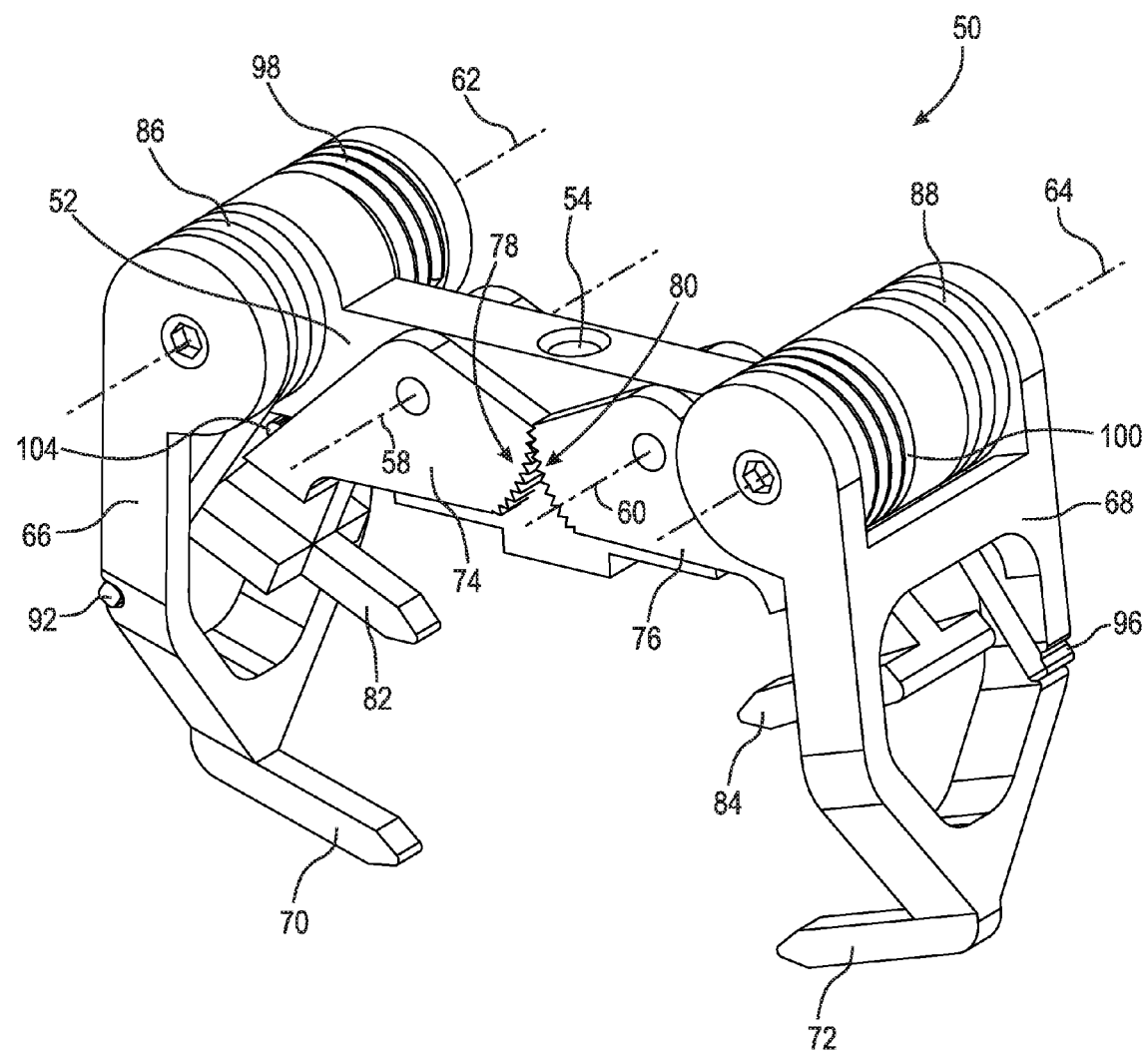
FIG. 4 is a perspective view of the present apparatus of FIG. 1 also shown in an open arrangement.
Figure 5:
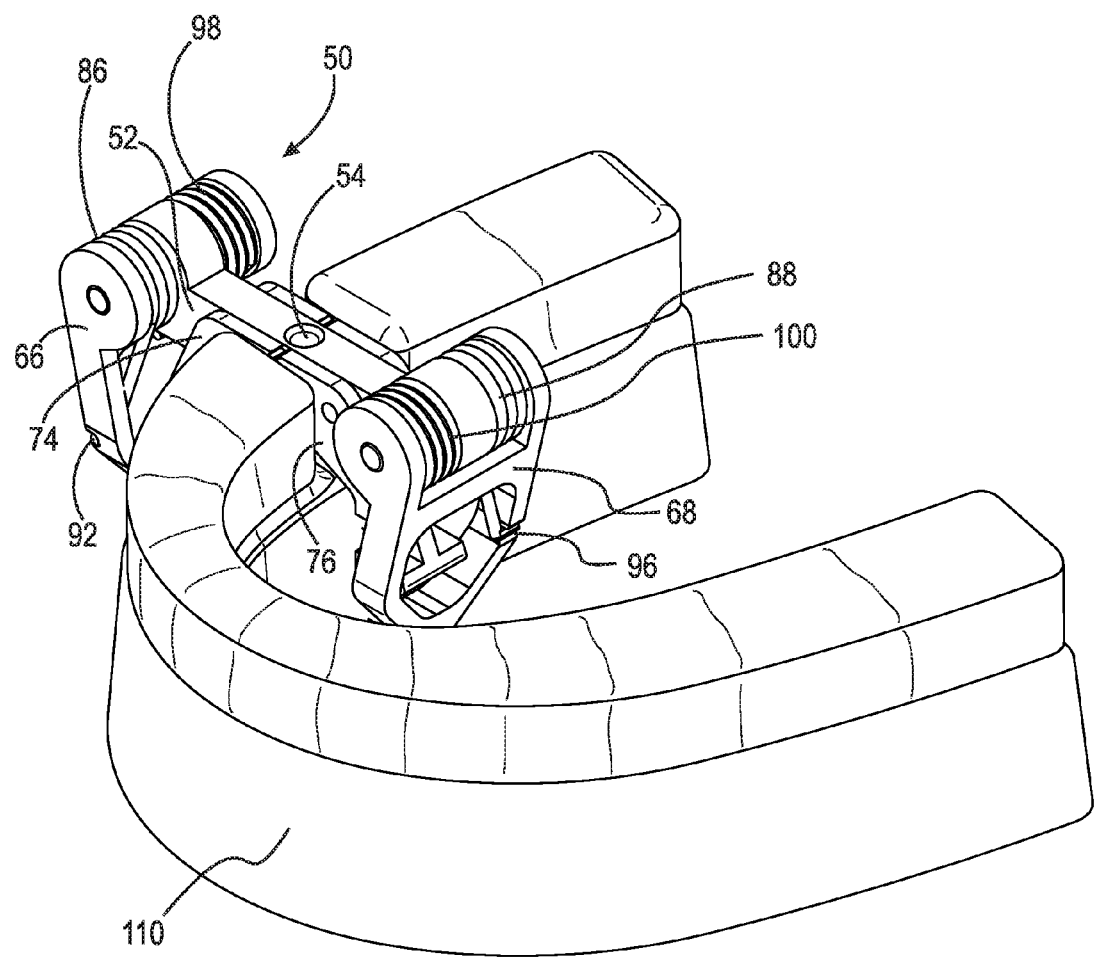
FIG. 5 is a perspective view of an embodiment of a present apparatus for aligning a dental drill shown positioned on a jawbone at the gum tissue in an opening between teeth; and, FIG. 6 is a side elevational view of an embodiment of a present apparatus for aligning a dental drill shown positioned on a jawbone with a dental drill aligned with the jawbone.
Figure 6:
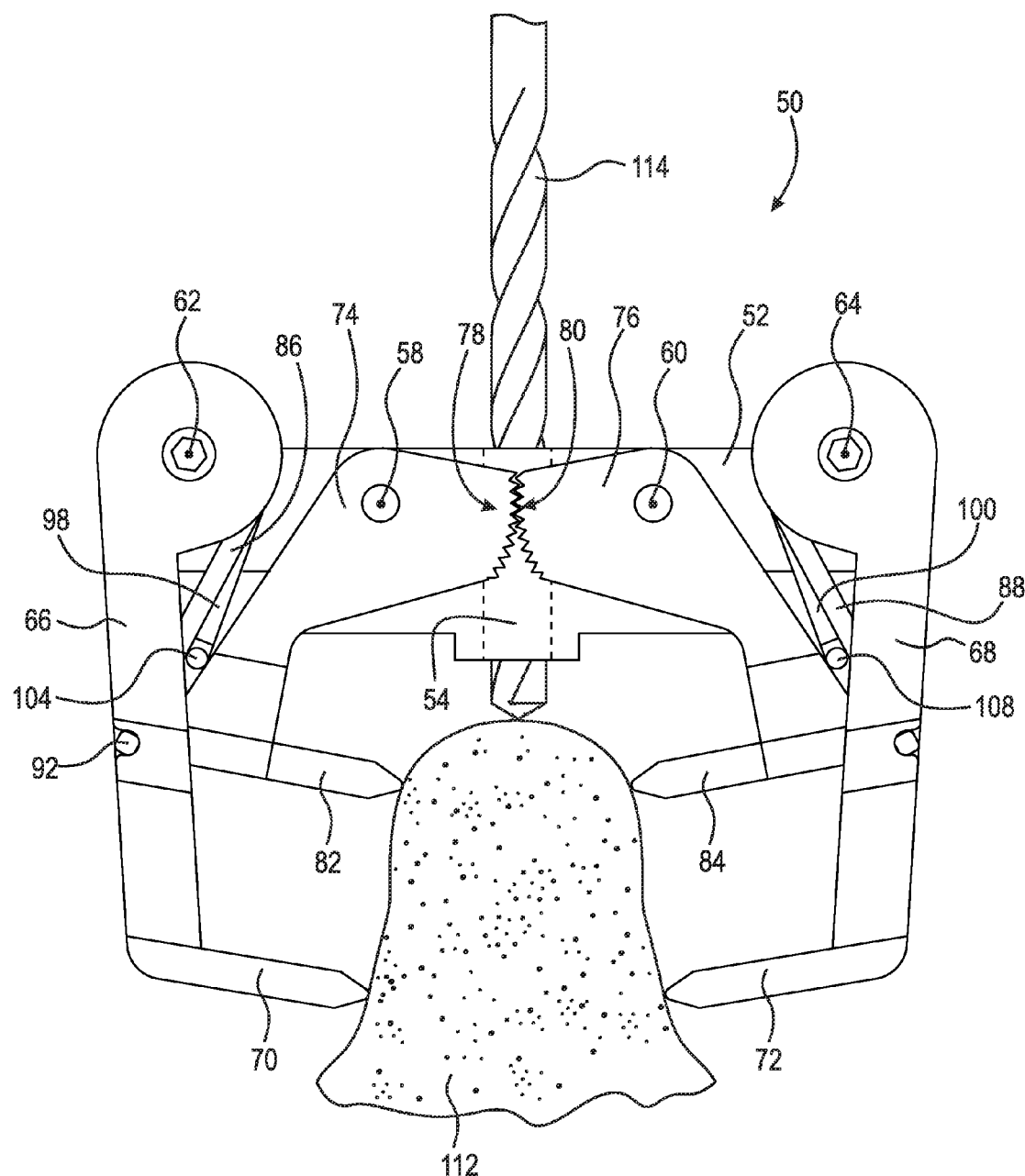

At the outset, it should be appreciated that like drawing numbers on different drawing views identify identical, or functionally similar, structural elements of the embodiments set forth herein. Furthermore, it is understood that these embodiments are not limited to the particular methodology, materials and modifications described and as such may, of course, vary. It is also understood that the terminology used herein is for the purpose of describing particular aspects only, and is not intended to limit the scope of the disclosed embodiments, which are limited only by the appended claims.

Unless defined otherwise, all technical and scientific terms used herein have the same meaning as commonly understood to one of ordinary skill in the art to which these embodiments belong.

Moreover, although any methods, devices or materials similar or equivalent to those described herein can be used in the practice or testing of these embodiments, some embodiments of methods, devices, and materials are now described.

Embodiments of a present apparatus for aligning a dental drill are depicted in the accompanying figures. Apparatus 50 comprises guide body 52. Guide body 52 comprises drill guide through hole 54 having longitudinal axis 56, a pair of guide pincer axes orthogonal to and symmetrical about the longitudinal axis, i.e., guide pincer axes 58 and 60, and a pair of outer pincer axes orthogonal to and symmetrical about the longitudinal axis, i.e., outer pincer axes 62 and 64. Apparatus 50 further comprises a pair of opposed outer pincers 66 and 68. Each outer pincer comprises an outer engagement protrusion, i.e., outer pincers 66 and 68 comprise outer engagement protrusions 70 and 72, respectively. Each outer pincer is rotatable about a respective one of the pair of outer pincer axes. For example, outer pincer 66 rotates about outer pincer axis 62, while outer pincer 68 rotates about outer pincer axis 64. Apparatus 50 still further comprises a pair of opposed guide pincers 74 and 76. In some embodiments, each guide pincer comprises gear teeth, e.g., gear teeth 78 and 80, and a guide engagement protrusion, e.g., guide engagement protrusions 82 and 84. Each guide pincer is rotatable about a respective one of the pair of guide pincer axes. For example, guide pincer 74 rotates about guide pincer axis 58, while guide pincer 76 rotates about guide pincer axis 60.

Gear teeth 78 of guide pincer 74 engage gear teeth 80 of guide pincer 76. Due to the interaction of gear teeth 78 with gear teeth 80, rotation of guide pincer 74 causes rotation of guide pincer 76. Outer pincers 66 and 68 rotate independent of each other, i.e., the rotation of outer pincer 66 does not cause rotation of outer pincer 68. It should be appreciated that other embodiments are also possible. For example, guide pincers 74 and 76 may independently rotate relative to each other, i.e., no gear teeth are included on one or both of guide pincers 74 and 76 or, alternatively, gear teeth 78 do not engage gear teeth 80. Such embodiments, fall within the scope of the claims included herebelow.

In some embodiments, apparatus 50 further comprises a pair of outer pincer springs, such as springs 86 and 88. Each of springs 86 and 88 comprises a first end and a second end. Thus, spring 86 comprises a first end (not shown) and second end 92, while spring 88 comprises a first end (not shown) and second end 96. The first end (not shown) of outer pincer spring 86 contacts guide body 52, while the second end 92 of outer pincer spring 86 contacts outer pincer 66. Similarly, the first end (not shown) of outer pincer spring 88 contacts guide body 52, while second end 96 of outer pincer spring 88 contacts outer pincer 68. It should be appreciated that the first ends of springs 86 and 88 contact guide body 52 via conventional means, e.g., similar to the contact depicted for the second ends of springs 86 and 88 or each first end may be received within respective bores in guide body 52, which respective bores are concealed from view by the coiled portions of springs 86 and 88. It should be further appreciated that although springs 86 and 88 are depicted in the form of a conventional coiled torsion spring, other springs may be used, e.g., a tension spring, and such variations fall within the scope of the claims below.

In some embodiments, apparatus 50 further comprises a pair of guide pincer springs, such as springs 98 and 100. Each of springs 98 and 100 comprises a first end and a second end. Thus, spring 98 comprises a first end (not shown) and second end 104, while spring 100 comprises a first end (not shown) and second end 108. The first end (not shown) of guide pincer spring 98 contacts guide body 52, while second end 104 of guide pincer spring 98 contacts guide pincer 74. Similarly, the first end (not shown) of guide pincer spring 100 contacts guide body 52, while second end 108 of guide pincer spring 100 contacts guide pincer 76. It should be appreciated that the first ends of springs 98 and 100 contact guide body 52 via conventional means, e.g., similar to the contact depicted for the second ends of springs 98 and 100 or each first end may be received within respective bores in guide body 52, which respective bores are concealed from view by the coiled portions of springs 98 and 100. It should be further appreciated that although springs 98 and 100 are depicted in the form of a conventional coiled torsion spring, other springs may be used, e.g., a tension spring, and such variations fall within the scope of the claims below. Moreover, it should be appreciated that for embodiments comprising gear teeth 78 and 80, only a single spring acting on either guide pincer 74 or 76, i.e., the biasing force of the single spring is imparted on one of the guide pincers, and transmitted to the other guide pincer via the interaction of the gear teeth.

In some embodiments, apparatus 50 further comprises both a pair of outer pincer springs and a pair of guide pincer springs. In those embodiments, the arrangement of outer pincer springs 86 and 88 relative to guide body 52 and outer pincers 66 and 68, and guide pincer springs 98 and 100 relative to guide body 52 and guide pincers 74 and 76 is in accordance with the arrangements described above.

In some embodiments, guide engagement protrusions 82 and 84 contact a patient's gum tissue, e.g., gum tissue 110, and/or a patient's jawbone, e.g., jawbone 112. Similarly, in some embodiments, outer engagement protrusions 70 and 72 contact a patient's gum tissue, e.g., gum tissue 110, and/or a patient's jawbone, e.g., jawbone 112. It has been found that apparatus 50 performs sufficiently to align dental drill 114 in embodiments where guide engagement protrusions 82 and 84 are positioned between the region of jawbone 112 closest to the teeth and outer engagement protrusions 70 and 72. It should be appreciated that other embodiments are also possible, such as the opposite arrangement of guide engagement protrusions 82 and 84 relative to outer engagement protrusions 70 and 72. It should be further appreciated that some or all of the outer pincers and guide pincers may comprise more than a single engagement protrusion as depicted in the accompanying figures. For example, each pincer may include two engagement protrusions, or alternatively, opposed pincers may comprise one protrusion and two protrusions, respectively. Such variations of the pincers and engagement protrusions fall within the scope of the claims below.

The embodiments of the present apparatus described above align a dental drill relative to a jawbone so that misaligned drilling, e.g., drilling through the side of the jawbone are prevented. The interaction between the outer pincers and the guide pincers align the drill guide to the shape of the overall jawbone, and in particular, account for irregularities in shape, size and thickness of the region of the jawbone where teeth are located.

It will be appreciated that various of the above-disclosed and other features and functions, or alternatives thereof, may be desirably combined into many other different systems or applications. Various presently unforeseen or unanticipated alternatives, modifications, variations or improvements therein may be subsequently made by those skilled in the art which are also intended to be encompassed by the following claims.

What is claimed is:

1. An apparatus for aligning a dental drill comprising:
a guide body comprising a drill guide through hole having a longitudinal axis, a pair of guide pincer axes orthogonal to and symmetrical about the longitudinal axis and a pair of outer pincer axes orthogonal to and symmetrical about the longitudinal axis;
a pair of opposed outer pincers, each outer pincer comprising an outer engagement protrusion, and each outer pincer is rotatable about a respective one of the pair of outer pincer axes; and,
a pair of opposed guide pincers, each guide pincer comprising gear teeth and a guide engagement protrusion, and each guide pincer is rotatable about a respective one of the pair of guide pincer axes,
wherein the gear teeth of each guide pincer engage the gear teeth of the other guide pincer, rotation of one of the pair of guide pincers causes rotation of the other of the pair of guide pincers and the pair of opposed outer pincers rotate independent of each other.

2. The apparatus of claim 1 further comprising:
a pair of outer pincer springs each comprising a first end and a second end,
wherein the first end of each of the pair of outer pincer springs contacts the guide body and the second end of each of the pair of outer pincer springs contacts a respective one of the pair of outer pincers.

3. The apparatus of claim 1 further comprising:
a pair of guide pincer springs each comprising a first end and a second end,
wherein the first end of each of the pair of guide pincer springs contacts the guide body and the second end of each of the pair of guide pincer springs contacts a respective one of the pair of guide pincers.

4. The apparatus of claim 1 further comprising:
a guide pincer spring comprising a first end and a second end,
wherein the first end of the guide pincer spring contacts the guide body and the second end of the guide pincer spring contacts one of the pair of guide pincers.

5. The apparatus of claim 1 further comprising:
a pair of outer pincer springs each comprising a first end and a second end,
a pair of guide pincer springs each comprising a first end and a second end,
wherein the first end of each of the pair of outer pincer springs contacts the guide body, the second end of each of the pair of outer pincer springs contacts a respective one of the pair of outer pincers, the first end of each of the pair of guide pincer springs contacts the guide body and the second end of each of the pair of guide pincer springs contacts a respective one of the pair of guide pincers.

6. The apparatus of claim 1 wherein each of the guide engagement protrusions and each of the outer engagement protrusions is adapted to contact a patient gum tissue, is adapted to contact a patient jawbone or is adapted to contact the patient gum tissue and the patient jawbone.

7. An apparatus for aligning a dental drill comprising:
a guide body comprising a drill guide through hole having a longitudinal axis, a pair of guide pincer axes orthogonal to and symmetrical about the longitudinal axis and a pair of outer pincer axes orthogonal to and symmetrical about the longitudinal axis;
a pair of opposed outer pincers, each outer pincer comprising an outer engagement protrusion, and each outer pincer is rotatable about a respective one of the pair of outer pincer axes; and,
a pair of opposed guide pincers, each guide pincer comprising a guide engagement protrusion, and each guide pincer is rotatable about a respective one of the pair of guide pincer axes,
wherein the pair of opposed outer pincers rotate independent of each other and the pair of opposed guide pincers rotate independent of each other.

8. The apparatus of claim 7 further comprising:
a pair of outer pincer springs each comprising a first end and a second end,
wherein the first end of each of the pair of outer pincer springs contacts the guide body and the second end of each of the pair of outer pincer springs contacts a respective one of the pair of outer pincers.

9. The apparatus of claim 7 further comprising:
a pair of guide pincer springs each comprising a first end and a second end,
wherein the first end of each of the pair of guide pincer springs contacts the guide body and the second end of each of the pair of guide pincer springs contacts a respective one of the pair of guide pincers.

10. The apparatus of claim 7 further comprising:
a pair of outer pincer springs each comprising a first end and a second end,
a pair of guide pincer springs each comprising a first end and a second end,
wherein the first end of each of the pair of outer pincer springs contacts the guide body, the second end of each of the pair of outer pincer springs contacts a respective one of the pair of outer pincers, the first end of each of the pair of guide pincer springs contacts the guide body and the second end of each of the pair of guide pincer springs contacts a respective one of the pair of guide pincers.

11. The apparatus of claim 7 wherein each of the guide engagement protrusions and each of the outer engagement protrusions is adapted to contact a patient gum tissue, is adapted to contact a patient jawbone or is adapted to contact the patient gum tissue and the patient jawbone.

* * * * *